(12) United States Patent
Sim et al.

(10) Patent No.: US 7,776,554 B2
(45) Date of Patent: Aug. 17, 2010

(54) COLORIMETRIC SENSOR USING POLYDIACETYLENE SUPRAMOLECULE

(75) Inventors: Sang-jun Sim, Seoul (KR); Sang-wook Lee, Seoul (KR); Dong June Ahn, Seoul (KR); Doo ho Yang, Seoul (KR)

(73) Assignee: Sungkyunkwan University, Seoul (KR)

( * ) Notice: Subject to any disclaimer, the term of this patent is extended or adjusted under 35 U.S.C. 154(b) by 529 days.

(21) Appl. No.: 11/639,241

(22) Filed: Dec. 15, 2006

(65) Prior Publication Data

US 2007/0275371 A1    Nov. 29, 2007

(30) Foreign Application Priority Data

Dec. 16, 2005    (KR) .................... 10-2005-0124361

(51) Int. Cl.
*G01N 33/53* (2006.01)
*G01N 33/551* (2006.01)
*G01N 33/544* (2006.01)
*G01N 21/76* (2006.01)
*C12P 7/40* (2006.01)

(52) U.S. Cl. .............. 435/7.1; 435/7.2; 435/7.92; 435/136; 436/524; 436/528; 436/172

(58) Field of Classification Search .............. None
See application file for complete search history.

(56) References Cited

U.S. PATENT DOCUMENTS 5,156,810 A * 10/1992 Ribi ................. 422/82.01
6,277,652 B1 * 8/2001 Jo et al. ................. 436/518

* cited by examiner

*Primary Examiner*—Shafiqul Haq
(74) *Attorney, Agent, or Firm*—Kenyon & Kenyon LLP

(57) ABSTRACT

There is provided a polydiacetylene supramolecule comprising diacetylene molecules, capable of immobilizing a receptor molecule having a thiol group. Since the polydiacetylene supramolecule has a receptor immobilized thereon having a thiol group, for example, an antibody, and thus shows color transition when reacting with a sample, an antigen can be detected through specific color transition of the polydiacetylene when employing in a receptor-ligand reaction, for example, an antibody-antigen reaction.

7 Claims, 2 Drawing Sheets

Formula III

Formula IV

COLORIMETRIC SENSOR USING POLYDIACETYLENE SUPRAMOLECULE

CROSS-REFERENCE TO RELATED APPLICATION

This application claims the benefit of Korean Patent Application No. 10-2005-0124361, filed Dec. 16, 2005, the disclosure of which is hereby incorporated herein by reference in its entirety.

BACKGROUND OF THE INVENTION

1. Technical Field

The present invention relates to a calorimetric sensor in which a receptor is immobilized on polydiacetylene supramolecule and, more particularly, to biochemical analysis using the same.

2. Discussion of Related Art

A general quantitative analysis utilizing an antibody includes enzyme immunoassay (EI), enzyme-linked immunosorbent assay (ELISA) and radio immunoassay (RIA). Of these, ELISA is a method that an enzyme is linked to an antibody and then an antigen-antibody reaction is identified. ELISA is now widely used since it is relatively simple and inexpensive, and is available to massive analysis. Particularly, ELISA is increasingly employed since it has a great advantage in that it has a sensitivity equal to that of RIA, but does not use radioactivity. However, ELISA has disadvantages in that it requires more samples in analysis, it takes long time, and it must undergo several steps. Further, although RIA has the highest sensitivity, it has a problem of danger due to radioactive materials.

Recently, in order to solve such problems, there have been suggested analytical methods that employ an isotope, fluorescence or an enzymatic reaction, and can convert a signal. However, of these methods, the method employing an isotope has a problem in safety, the method employing an enzymatic reaction has narrow analytical range and thus is not suitable for analyzing a sample in various concentration, and the method employing fluorescence has a problem that expensive fluorescent material must be again bound to a detected protein. In order to solve such problems, a label-free detecting method, for example, a method employing polydiacetylene, was suggested.

Polydiacetylene refers to a polymer of diacetylene monomers having alternate triple bonds. It is known that diacetylene forms a supramolecule such as a liposome, a langmuir-blodgett (LB) or langmuir-schaeffer (LS) single molecular membrane in an aqueous solution due to its amphoteric property. When the diacetylene constituting a supramolecule is exposed to UV light at 254 nm, polymerization between adjacent diacetylenes occurs and thus the diacetylene becomes blue. Further, when a polymerized polydiacetylene supramolecule is stimulated by temperature, pH, friction, a surfactant or a solvent, etc., its color is transited into red one. Polydiacetylene color transition is dependent on the length of $\pi$-conjugation in a polymeric bond, and a structure of the resulting molecule. Accordingly, various types of sensors can be prepared by employing the change in a polydiacetylene polymeric bond. For example, a biosensor capable of detecting an influenza virus, a cholera toxin, or $E.\ coli$, etc. can be prepared by introducing chemically a molecule capable of binding specifically to a cell or a protein into a terminal group of a diacetylene or other lipid molecule, and then mixing it with other diacetylene to form a liposome. However, the polydiacetylene biosensor has a disadvantage in that a lipid molecule having receptor function must be newly synthesized depending on an analyte.

Thus, the present inventors completed the present invention by preparing a polydiacetylene supramolecule with use of a diacetylene-maleimide molecule capable of reacting quickly and selectively with thiol, selecting an antibody or other receptor suitable for an analyte and immobilizing it on the polydiacetylene, and then reacting it with a sample containing an antigen or a ligand thereby confirming color transition of the polydiacetylene supramolecule.

SUMMARY OF THE INVENTION

Therefore, the present invention is directed to provide a polydiacetylene supramolecule capable of immobilizing a receptor molecule having a thiol group.

Another object of the present invention is to provide a polydiacetylene supramolecule based sensor in which a thiol based receptor suitable for an objective material (ligand) to be detected is immobilized on the polydiacetylene supramolecule.

Still another object of the present invention is to provide a biochemical analysis of detecting an objective material by reacting a polydiacetylene supramolecule based sensor with a sample containing an objective material (ligand) to be detected.

In accordance with an exemplary embodiment, the present invention provides a polydiacetylene supramolecule, such as a liposome, a micell, a LB film and a LS film, comprising a diacetylene monomer represented by formula I below having —COOH end and a diacetylene monomer represented by formula II below having a lipid molecule capable of reacting with a thiol:

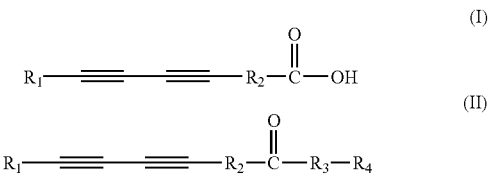

In the formulas, $R_1$ is a $C_1$ to $C_{10}$ alkyl group, $R_2$ is a $C_1$ to $C_{10}$ alkyl group, $R_3$ is

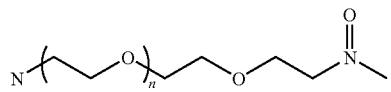

wherein n represents an integer of 1 to 10, and $R_4$ is

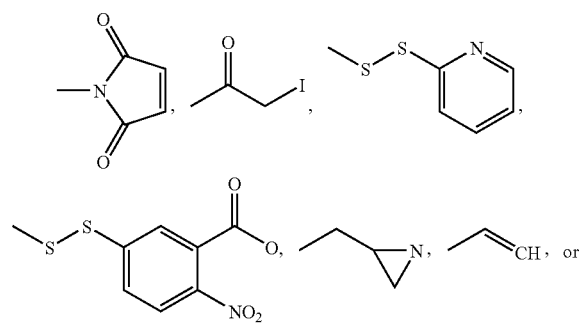

-continued

[Structure F: ethyl-substituted benzene ring with F substituent]

Further, the diacetylene monomer in the present invention may include 10,12-pentacosadiynoic acid, 5,7-eicosadiynoic acid, 2,4-heptacosadiynoic acid or a mixture thereof, but the terminal group is not limited to —COOH. Further, the terminal group of the lipid molecule in the present invention may include maleimide, iodoacetyl, aziridine, acryloyl, fluorobenzene, TNB-thiol, and dithiopyridine.

In accordance with another exemplary embodiment, the present invention provides a polydiacetylene supramolecule in which a receptor having a thiol group is immobilized on surface by a thioester bond or a disulfide bond. The receptor in the present invention may include an antibody, a monoclonal antibody, F(ab), F(ab)'2, an aptamer, a protein, a peptide, a carbohydrate, an antigen, or a mixture of more than one of these.

In accordance with another exemplary embodiment, a receptor having a thiol group may be immobilized on its surface by a thioester bond or a disulfide bond.

In accordance with another exemplary embodiment, the present invention provides a biochemical biosensor and its analytical technique comprising: (a) preparing a supramolecule, such as a liposome, a micell, a LB film or a LS film, formed by mixing a diacetylene monomer represented by the formula I having —COOH end and a diacetylene monomer represented by the formula II having a lipid molecule capable of reacting with a thiol group in a specific ratio, (b) exposing a thiol group to a receptor by reacting the receptor such as an antibody with a reducing agent to oxidize disulfide, or introducing a thiol group by a chemical reaction, (c) immobilizing the receptor on the supramolecule by reacting the reduced receptor such as an antibody with the supramolecule to induce a thioester bond between the thiol group of the receptor and the lipid molecule of the supramolecule, (d) polymerizing the supramolecule by irradiating UV light at 254 nm, and (e) contacting the supramolecule with the sample and then observing color transition to analyze the presence of the ligand in the sample qualitatively and quantitatively.

In accordance with another exemplary embodiment, the present invention provides a polydiacetylene biosensor, i.e., a biosensor in which a receptor is immobilized on polydiacetylene supramolecule by employing a diacetylene or lipid molecule capable of binding chemically to thiol, and a biochemical analysis or diagnosis using the same.

BRIEF DESCRIPTION OF THE DRAWINGS

The above and other features and advantages of the present invention will become more apparent to those of ordinary skill in the art by describing in detail preferred embodiments thereof with reference to the attached drawings in which.

DETAILED DESCRIPTION OF THE INVENTION

Figure 1:
FIG. 1 shows the structure of the diacetylene monomer of formula I.
Figure 2:
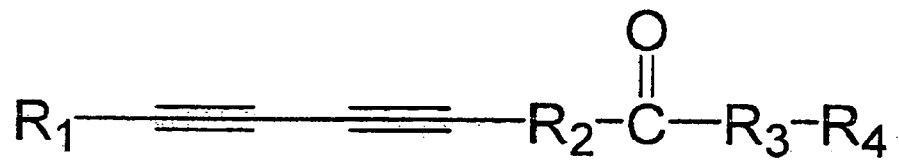
FIG. 2 shows the structure of the diacetylene monomer of formula II.
Figure 3:
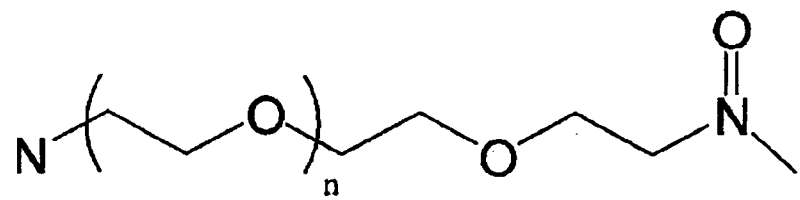
FIG. 3 shows the structure of diacetylene monomer 10,12-pentacosadiynoic acid (PCDA) of formula III.
Figure 4:
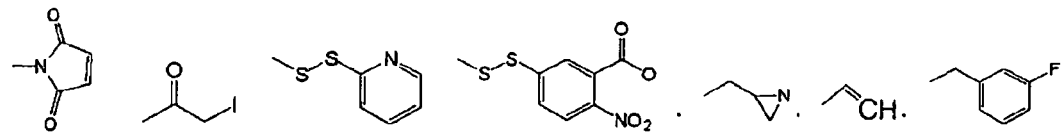
FIG. 4 shows some examples of the lipid molecules capable of reacting with thiol groups.

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided as teaching examples of the invention. Like numbers refer to like element.

The present invention employs diacetylene synthesized chemically, having a lipid molecule such as maleimide capable of reacting with thiol on its terminal group. Since amphoteric diacetylene forms interface with an aqueous solution by its amphoteric property, its self assembly can be induced by a supramolecule such as a liposome, a micell, a Langmuir Blodgett or Langmuir Schaeffer film. If the distance between the diacetylene monomers is sufficiently narrow when forming a supramolecule, the acetylenes can be polymerized with UV light at 254 nm, thereby showing blue color by newly formed polymeric bond. The color of the polymeric bond is closely related to π-conjugation participating in binding. That is, rearrangement of monomers in a polymer occurs by external stimulus thereby shortening π-conjugation and then showing gradually transition to red color depending on the degree of the stimulus. The general stimulus capable of inducing color transition includes temperature, pH, surface friction, and interaction with an organic solvent or a surfactant. In addition, when the monomers of the supramolecule are chemically modified so that a receptor is exposed to the interface of the supramolecule, the supramolecule can be employed as a biosensor or a biochemical analytic technique since the receptor reacts with the ligand to induce color transition.

The present invention provides a polydiacetylene supramolecule, such as a liposome, a micell, a LB film and a LS film, comprising a diacetylene monomer represented by formula I below having —COOH end and a diacetylene monomer represented by formula II below having a lipid molecule capable of reacting with a thiol:

$$R_1 \equiv\equiv\equiv\equiv R_2 - \overset{O}{\underset{\|}{C}} - OH \quad (I)$$

$$R_1 \equiv\equiv\equiv\equiv R_2 - \overset{O}{\underset{\|}{C}} - R_3 - R_4 \quad (II)$$

In the formulas, $R_1$ is a $C_1$ to $C_{10}$ alkyl group, $R_2$ is a $C_1$ to $C_{10}$ alkyl group, $R_3$ is

[Structure showing: N—(CH₂CH₂—O)ₙ—CH₂CH₂—O—CH₂CH₂—N with C=O group]

wherein n represents an integer of 1 to 10, and $R_4$ is

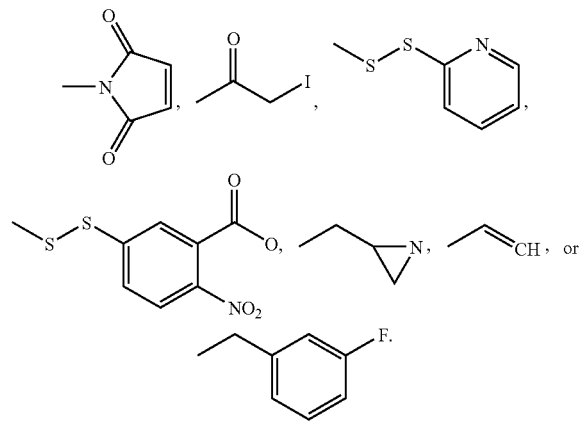

In an exemplary embodiment, the sensitivity of the sensor can be controlled by controlling the length of a spacer ($R_3$ in the formula) in the molecule that reacts with thiol in the polydiacetylene supramolecule.

In accordance with another exemplary embodiment, the present invention provides a polydiacetylene supramolecule in which a receptor having a thiol group is immobilized on surface by a thioester bond or a disulfide bond. The receptor in the present invention includes an antibody, a monoclonal antibody, F(ab), F(ab)'2, an aptamer, a protein, a peptide, a carbohydrate, an antigen, or a mixture of more than one of these.

In accordance with another exemplary embodiment, the present invention provides a biochemical biosensor and its analytical technique comprising: (a) preparing a supramolecule, such as a liposome, a micell, a LB film or a LS film, formed by mixing a diacetylene monomer represented by the formula I having —COOH end and a diacetylene monomer represented by the formula II having a lipid molecule capable of reacting with a thiol group in a specific ratio, (b) exposing a thiol group to a receptor by reacting the receptor such as an antibody with a reducing agent to oxidize disulfide, or introducing a thiol group by a chemical reaction, (c) immobilizing the receptor on the supramolecule by reacting the reduced receptor such as an antibody with the supramolecule to induce a thioester bond between the thiol group of the receptor and the lipid molecule of the supramolecule, (d) polymerizing the supramolecule by irradiating UV light at 254 nm, and (e) contacting the supramolecule with the sample and then observing color transition to analyze the presence of the ligand in the sample qualitatively and quantitatively.

In an exemplary embodiment, the ligand includes a bacteria, a pathogenic microorganism, a virus, a protein, a toxin, a peptide, a hormone, an enzyme, a toxic compound or a mixture of more than one of these.

Accordingly, in accordance with another exemplary embodiment, the present invention provides a polydiacetylene biosensor, i.e., a biosensor in which a receptor is immobilized on polydiacetylene supramolecule by employing a diacetylene or lipid molecule capable of binding chemically to thiol, and a biochemical analysis or diagnosis using the same.

Further, the analysis of a sample employing the polydiacetylene supramolecule according to an exemplary embodiment can be performed in a micro-well plate.

The present invention will be described in greater detail with reference to the following examples. However, the following examples are for illustrative purposes only and are not intended to limit the scope of the invention.

EXAMPLES

A Method of Detecting a Pathogenic Bacteria Employing a Polydiacetylene Liposome and an Antibody in a Liquid State Example 1

Preparation of a Liposome

PCDA and PCDA-maleimide diacetylene monomer were mixed in ratios of 1:9, 2:8 or 3:7 in chloroform in a vitreous bottle, and then chloroform was evaporated with nitrogen gas or by rotary evaporation to form a thin film consisting of the two components. Then, the film was soaked in 10 mM HEPES buffer (pH=7.4) and they are shaken slowly for 15 minutes at high temperature of above 80° C., and then the film was treated by probe sonication for 20 minutes at 30 W. Thus prepared liposome was stored for about 4 hours in a refrigerator, and then was used in next experiment.

Example 2

Reduction and Immobilization of an Antibody

A monoclonal antibody (Waterborne Inc., USA) against 0.3 mg/ml of *Cryptosporidium parvum* was mixed with 20 mM TCEP (Tris 2-carboxyethyl phosphine) at ratio of 1:1, and then the mixture was reacted for 1 hour at room temperature. Buffer exchange was performed with HEPES buffer containing 0.02 mM TCEP by employing 30 kDa MWCO (molecular weight of fraction) filter available at Amicon. The antibody treated according to such method was mixed with the liposome solution of the Example 1 to final concentration of 0.1 mg/ml and then the mixture was reacted for 3 hours at room temperature. Then, L-cysteine was added to final concentration of 1 mM and then the remaining maleimide functional group of the liposome was capped.

Example 3

Detection of a Pathogenic Bacteria Employing an Antibody-immobilized Liposome

Figure 5:
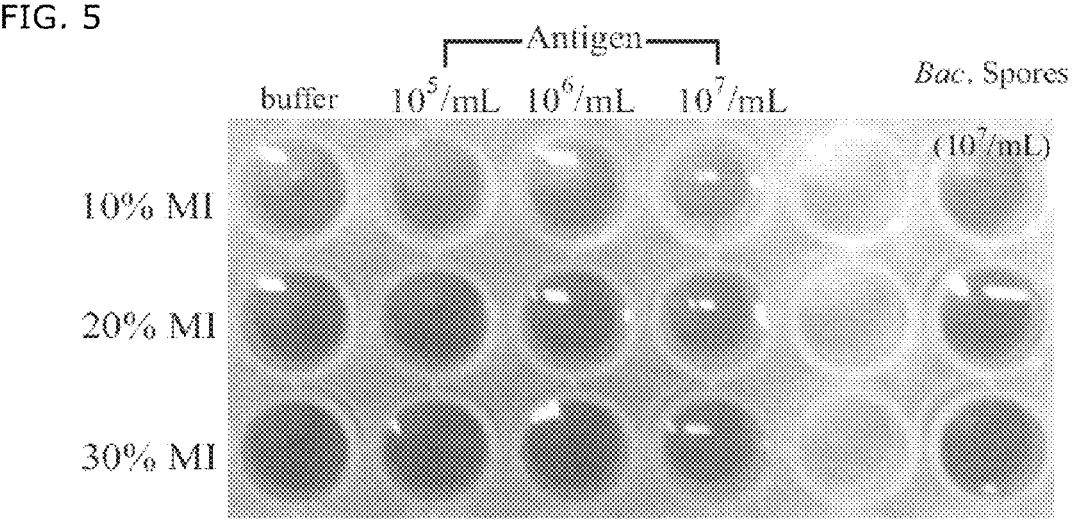
FIG. 5 shows a biosensor in which a monoclonal antibody against *Cryptosporidium parvum* is bound to a polydiacetylene liposome.

When an antibody-polydiacetylene liposome was exposed to UV light at 254 nm, it was confirmed that a blue solution was generated. When 50 µl of the solution and 100 µl of HEPES buffer containing *C. parvum* were mixed and reacted for 2.5 hours at 37° C., it was observed that the color of the antibody-polydiacetylene liposome was changed from blue to violet or red depending on the concentration of *C. parvum* (FIG. 5). Columns 1~3 in FIG. 5 represent liposome sensors containing 10, 20 and 30 mol % of PCDA-maleimide, respectively. Row 1 represents color reaction of the liposome against a buffer, rows 2~4 represent color reaction of the liposome against a buffer containing $10^5$, $10^6$ and $10^7$/ml of *C. parvum*, respectively, and row 6 represents color reaction of the liposome against a buffer containing $10^7$/ml of *Bacillus* spore.

Figure 6:
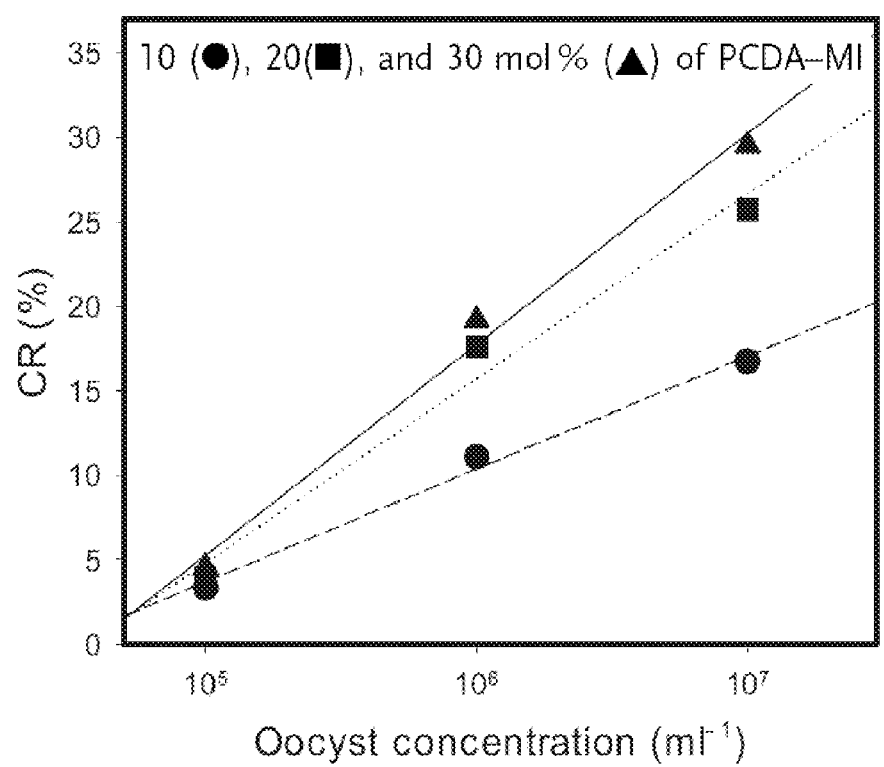
FIG. 6 is a graph expressing numerically (in percentage) the change in color of a biosensor in which a monoclonal antibody against *Cryptosporidium parvum* is bound to the polydiacetylene liposome.

FIG. 6 shows standard graph about the concentration of the ligand, expressed numerically concerning the solutions of the photographs in FIG. 5. Colorimetric response (CR) can be expressed numerically as follows by calculating relative values of absorption peak near 550 nm and 650 nm after scanning an area of 400 to 700 nm with UV-Vis Spectrometer:

$$CR(\%) = 100 \times \frac{B_0 - B_A}{B_0}, \text{ where } B = \frac{A_{650} - A_{550}}{A_{650}}$$

In the formula, B represents color index, and $B_O$ and $B_A$ represent the color index before and after adding an analyte, respectively. In creating the color index, $A_{650}$ and $A_{550}$ refer to maximum optical density of absorption peak near 650 nm and 550 nm.

As shown in FIG. 6, it was confirmed that the sensitivity of the biosensor is enhanced as the concentration (mol %) of PCDA-maleimide increases. This means that the sensitivity of the sensor employing the polydiacetylene supramolecule is dose-dependently proportional to the molar ratio of the lipid molecule capable of reacting with thiol in the polydiacetylene supramolecule. In FIG. 6, the transverse axis represents the Oocyst concentration of *C. parvum*, and the vertical axis represents the degree of color transition expressed numerically according to the numerical formula. In FIG. 6, ▲ represents a liposome sensor containing 30 mol % of PCDA-maleimide, ■ represents a liposome sensor containing 20 mol % of PCDA-maleimide, and ● represents a liposome sensor of 10 mol % PCDA-maleimide, respectively.

Thus, the polydiacetylene supramolecule capable of immobilizing a receptor molecule having thiol group according to the present invention can be employed in detecting a ligand by immobilizing easily a suitable receptor on the surface of the polydiacetylene supramolecule. Therefore, according to the present invention, a receptor suitable for a ligand can be easily selected and employed in analyzing a sample.

The invention has been described using preferred exemplary embodiments. However, it is to be understood that the scope of the invention is not limited to the disclosed embodiments. On the contrary, the scope of the invention is intended to include various modifications and alternative arrangements within the capabilities of persons skilled in the art using presently known or future technologies and equivalents. The scope of the claims, therefore, should be accorded the broadest interpretation so as to encompass all such modifications and similar arrangements.

What is claimed is:

1. A method of detecting a ligand that reacts with a receptor immobilized on polydiacetylene from a sample, the method comprising steps of:

i) mixing a diacetylene monomer represented by formula I below and 20-30 mol % of a diacetylene monomer represented by formula II to form a polydiacetylene supramolecule of a liposome, a micelle, a Langmuir Blodgett film or a Langmuir Schaeffer film;

ii) immobilizing the receptor on the supramolecule by employing the thiol functional group of the receptor;

iii) polymerizing the supramolecule by irradiating UV light on the supramolecule of the above step ii); and iv) reacting the polymerized supramolecule of the above step iii) with the sample, wherein a color transition indicates the presence of the ligand in the sample, and wherein formula I and formula II are as follows:

(I)

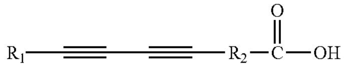

-continued (II)

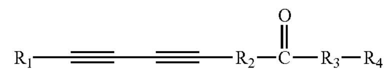

wherein $R_1$ is a $C_1$ to $C_{10}$ alkyl group, $R_2$ is a $C_1$ to $C_{10}$ alkyl group, $R_3$ is wherein n represents an integer of 1 to 10, and $R_4$ is 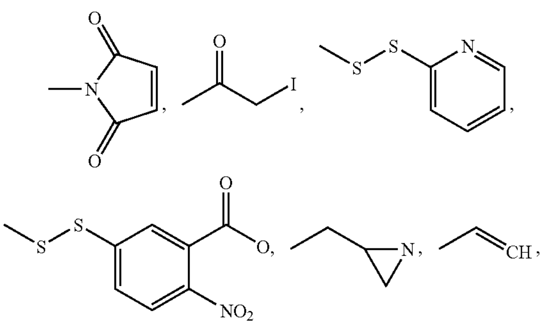 or

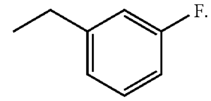

2. The method of detecting a ligand that reacts with a receptor immobilized on polydiacetylene from a sample according to claim 1, wherein the receptor is an antibody, a monoclonal antibody, F(ab), F(ab)'2, an aptamer, a protein, a peptide, a carbohydrate, an antigen, or a mixture of more than one of these.

3. The method of detecting a ligand that reacts with a receptor immobilized on polydiacetylene from a sample according to claim 1, wherein the ligand is a bacteria, a pathogenic microorganism, a virus, a protein, a toxin, a peptide, a hormone, an enzyme, a toxic compound or a mixture of more than one of these.

4. The method of detecting a ligand that reacts with a receptor immobilized on polydiacetylene from a sample according to claim 2, wherein the ligand is a bacteria, a pathogenic microorganism, a virus, a protein, a toxin, a peptide, a hormone, an enzyme, a toxic compound or a mixture of more than one of these.

5. The method of detecting a ligand that reacts with a receptor immobilized on polydiacetylene from a sample according to claim 1, wherein the reaction of the polymerized supramolecule and the sample is performed on a micro-well plate.

6. The method of detecting a ligand that reacts with a receptor immobilized on polydiacetylene from a sample according to claim 2, wherein the reaction of the polymerized supramolecule and the sample is performed on a micro-well plate.

7. The method of detecting a ligand that reacts with a receptor immobilized on polydiacetylene from a sample according to claim 2, wherein the color transition is dose-dependently proportional to molar ratios of the diacetylene monomer represented by formula II in the polydiacetylene supramolecule.

* * * * *